(12) United States Patent
Byron et al.

(10) Patent No.: US 10,595,745 B2
(45) Date of Patent: Mar. 24, 2020

(54) FORCE SENSING CATHETER WITH IMPEDANCE-GUIDED ORIENTATION

(71) Applicant: Boston Scientific Scimed Inc., Maple Grove, MN (US)

(72) Inventors: Mary M. Byron, Roseville, MN (US); Jacob I. Laughner, St. Paul, MN (US); Shibaji Shome, Arden Hills, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 515 days.

(21) Appl. No.: 15/418,098

(22) Filed: Jan. 27, 2017

(65) Prior Publication Data
US 2017/0215802 A1    Aug. 3, 2017

Related U.S. Application Data

(60) Provisional application No. 62/288,434, filed on Jan. 29, 2016.

(51) Int. Cl.
*A61B 5/00* (2006.01)
*A61B 5/042* (2006.01)
(Continued)

(52) U.S. Cl.
CPC ............ *A61B 5/065* (2013.01); *A61B 5/0422* (2013.01); *A61B 5/068* (2013.01); *A61B 5/6843* (2013.01);
(Continued)

(58) Field of Classification Search
CPC ..... A61B 5/6852; A61B 5/0422; A61B 5/742; A61B 5/065; A61B 18/1492;
(Continued)

(56) References Cited

U.S. PATENT DOCUMENTS 4,930,494 A   6/1990   Takehana et al.
5,238,005 A   8/1993   Imran
(Continued)

FOREIGN PATENT DOCUMENTS

DE   102009037044 A1   3/2011
EP       1169974 A1    1/2002
(Continued)

OTHER PUBLICATIONS

Rafael AL, Heist EK. Techniques to optimize catheter contact force during ablation of atrial fibrillation. J. Innov. Card Rhythm Manage . . . Apr. 2015;6:1990-5 (Year: 2015).*

(Continued)

*Primary Examiner* — Eun Hwa Kim
*Assistant Examiner* — James A Cipriano
(74) *Attorney, Agent, or Firm* — Faegre Drinker Biddle & Reath LLP

(57) ABSTRACT

A catheter adapted to determine a contact force, the catheter including a proximal segment, a distal segment, and an elastic segment extending from the proximal segment to the distal segment. The distal segment includes a plurality of tip electrodes including at least three radial electrodes disposed about a circumference of the distal segment. The radial electrodes are configured to output electrical signals indicative of a contact vector of the contact force. The elastic segment includes a force sensing device configured to output an electrical signal indicative of a magnitude of an axial component of the contact force, wherein the contact force is determined by scaling the magnitude of the axial component of the contact force by the contact vector.

12 Claims, 6 Drawing Sheets

(51) Int. Cl.
  *A61B 5/06* (2006.01)
  *A61B 90/00* (2016.01)
  *A61B 18/14* (2006.01)
  *A61B 18/00* (2006.01)

(52) U.S. Cl.
  CPC ............ *A61B 5/6852* (2013.01); *A61B 5/742* (2013.01); *A61B 18/1492* (2013.01); *A61B 90/06* (2016.02); *A61B 2018/00351* (2013.01); *A61B 2018/00577* (2013.01); *A61B 2090/064* (2016.02); *A61B 2090/067* (2016.02)

(58) Field of Classification Search
  CPC ........... A61B 2018/00577; A61B 2018/00351; A61B 90/06; A61B 2090/064–067; A61N 1/05; A61N 1/0504; A61N 1/0563; A61N 1/0585; A61N 1/0587; A61N 1/06; A61N 1/362–371; A61N 2001/083
  See application file for complete search history.

(56) References Cited

U.S. PATENT DOCUMENTS

| | | | |
|---|---|---|---|
| 5,293,869 A | 3/1994 | Edwards et al. | |
| 5,313,943 A | 5/1994 | Houser et al. | |
| 5,383,874 A | 1/1995 | Jackson et al. | |
| 5,471,982 A | 12/1995 | Edwards et al. | |
| 5,553,611 A | 9/1996 | Budd et al. | |
| 5,647,870 A | 7/1997 | Kordis et al. | |
| 5,836,990 A | 11/1998 | Li | |
| 5,904,680 A | 5/1999 | Kordis et al. | |
| 5,911,694 A | 6/1999 | Ikeda et al. | |
| 5,911,739 A | 6/1999 | Kordis et al. | |
| 5,968,040 A | 10/1999 | Swanson et al. | |
| 6,014,590 A | 1/2000 | Whayne et al. | |
| 6,152,899 A | 11/2000 | Farley et al. | |
| 6,165,169 A | 12/2000 | Panescu et al. | |
| 6,216,043 B1 | 4/2001 | Swanson et al. | |
| 6,371,928 B1 | 4/2002 | McFann et al. | |
| 6,695,808 B2 | 2/2004 | Tom | |
| 7,637,903 B2 | 12/2009 | Lentz et al. | |
| 7,658,715 B2 | 2/2010 | Park et al. | |
| 7,720,420 B2 | 5/2010 | Kajita | |
| 8,374,670 B2 | 2/2013 | Selkee | |
| 8,496,653 B2 | 7/2013 | Steinke | |
| 8,529,476 B2 | 9/2013 | Govari | |
| 8,911,382 B2 | 12/2014 | Hauck et al. | |
| 9,060,782 B2 | 6/2015 | Daniel et al. | |
| 9,125,565 B2 | 9/2015 | Hauck | |
| 9,486,272 B2 | 11/2016 | Bonyak et al. | |
| 9,510,786 B2 | 12/2016 | Gliner | |
| 9,974,608 B2 | 5/2018 | Gliner et al. | |
| 10,022,190 B2 | 7/2018 | Valsamis et al. | |
| 2003/0056599 A1 | 3/2003 | van Schoor et al. | |
| 2003/0069522 A1 | 4/2003 | Jacobsen et al. | |
| 2003/0130615 A1 | 7/2003 | Tom | |
| 2004/0176699 A1 | 9/2004 | Walker et al. | |
| 2005/0096647 A1 | 5/2005 | Steinke et al. | |
| 2006/0189896 A1 | 8/2006 | Davis et al. | |
| 2006/0235286 A1 | 10/2006 | Stone et al. | |
| 2007/0156209 A1 | 7/2007 | Laufer et al. | |
| 2007/0191829 A1 | 8/2007 | McGee et al. | |
| 2008/0015568 A1 | 1/2008 | Paul et al. | |
| 2008/0051704 A1 | 2/2008 | Patel et al. | |
| 2008/0161796 A1 | 7/2008 | Cao et al. | |
| 2008/0319350 A1 | 12/2008 | Wallace et al. | |
| 2009/0076476 A1 | 3/2009 | Barbagli et al. | |
| 2009/0076498 A1 | 3/2009 | Saadat et al. | |
| 2009/0099551 A1 | 4/2009 | Tung et al. | |
| 2009/0306650 A1 | 12/2009 | Govari et al. | |
| 2010/0063492 A1 | 3/2010 | Kahlert et al. | |
| 2010/0168557 A1* | 7/2010 | Deno ............... A61B 5/0422 600/424 |
| 2010/0168620 A1 | 7/2010 | Klimovitch et al. | |
| 2011/0144509 A1 | 6/2011 | Kahlert et al. | |
| 2011/0160556 A1* | 6/2011 | Govari ................ A61B 5/065 600/374 |
| 2012/0035495 A1 | 2/2012 | Gutfinger et al. | |
| 2012/0041295 A1 | 2/2012 | Schultz | |
| 2012/0259238 A1 | 10/2012 | Gunday et al. | |
| 2012/0265102 A1 | 10/2012 | Leo et al. | |
| 2012/0271135 A1 | 10/2012 | Burke et al. | |
| 2012/0283713 A1 | 11/2012 | Mihalik et al. | |
| 2012/0283714 A1 | 11/2012 | Mihalik et al. | |
| 2012/0283715 A1 | 11/2012 | Mihalik et al. | |
| 2013/0066220 A1 | 3/2013 | Weinkam et al. | |
| 2013/0172715 A1 | 7/2013 | Just et al. | |
| 2013/0289369 A1 | 10/2013 | Margolis | |
| 2013/0310702 A1 | 11/2013 | Reinders et al. | |
| 2014/0025069 A1 | 1/2014 | Willard et al. | |
| 2014/0031785 A1 | 1/2014 | Schwagten et al. | |
| 2014/0081264 A1 | 3/2014 | Fandrey et al. | |
| 2014/0128949 A1 | 5/2014 | Hollett et al. | |
| 2014/0276078 A1 | 9/2014 | Schweitzer et al. | |
| 2014/0276787 A1 | 9/2014 | Wang et al. | |
| 2015/0157400 A1 | 6/2015 | Gelbart et al. | |
| 2015/0190616 A1 | 7/2015 | Salvestro et al. | |
| 2015/0223757 A1 | 8/2015 | Werneth et al. | |
| 2015/0300895 A1 | 10/2015 | Matsudate et al. | |
| 2015/0351652 A1 | 12/2015 | Marecki et al. | |
| 2015/0351836 A1 | 12/2015 | Prutchi | |
| 2015/0369373 A1 | 12/2015 | Reith et al. | |
| 2016/0113582 A1 | 4/2016 | Altmann et al. | |
| 2016/0278852 A1 | 9/2016 | Sliwa et al. | |
| 2016/0296333 A1 | 10/2016 | Balachandran et al. | |
| 2016/0351292 A1 | 12/2016 | Toth et al. | |
| 2017/0035358 A1 | 2/2017 | Rankin | |
| 2017/0035991 A1 | 2/2017 | Rankin et al. | |
| 2017/0143416 A1 | 5/2017 | Guler et al. | |
| 2017/0165000 A1 | 6/2017 | Basu et al. | |
| 2017/0172509 A1 | 6/2017 | Hein et al. | |
| 2017/0199064 A1 | 7/2017 | Lozano | |
| 2017/0296084 A1 | 10/2017 | Blauer et al. | |
| 2018/0078218 A1 | 3/2018 | Moisa et al. | |
| 2018/0264225 A1 | 9/2018 | Sardari et al. | |
| 2018/0360533 A1 | 12/2018 | Olson | |
| 2019/0059818 A1 | 2/2019 | Herrera et al. | |

FOREIGN PATENT DOCUMENTS

| | | | |
|---|---|---|---|
| EP | 1803410 A1 | 7/2007 |
| EP | 2047797 A2 | 4/2009 |
| EP | 2172240 A1 | 4/2010 |
| EP | 2526887 A1 | 11/2012 |
| EP | 2662015 B1 | 11/2013 |
| EP | 2732760 A1 | 5/2014 |
| EP | 2862537 A1 | 4/2015 |
| WO | 1995010978 A1 | 4/1995 |
| WO | 2001070117 A2 | 9/2001 |
| WO | 2002021995 A2 | 3/2002 |
| WO | 2015069887 A1 | 5/2015 |

OTHER PUBLICATIONS

International Search Report and Written Opinion issued in PCT/US2017015426, dated May 10, 2017, 13 pages.
Hoffmayer, K.S., et al. "Contact Force-Sensing Catheters." Current Opinion in Cardiology, 30(1):74-80, Jan. 2015.
International Search Report and the Written Opinion issued in PCT/US2016/045303, dated Oct. 20, 2016, 15 pages.
International Search Report and Written Opinion issued in PCT/US2016/045907, dated Oct. 20, 2016, 10 pages.
International Search Report and Written Opinion issued in PCT/US2016/062976, dated Feb. 8, 2017, 12 pages.
International Search Report and Written Opinion issued in PCT/US2016/067629, dated Mar. 17, 2017, 13 pages.
Internatilonal Preliminary Report on Patentability issued in PCT/US2016/045303, dated Feb. 22, 2018, 9 pages.
International Preliminary Report on Patentability issued in PCT/US2016/045907, dated Feb. 22, 2018, 7 pages.
International Preliminary Report on Patentability issued in PCT/US2016/062976, dated May 31, 2018, 8 pages.

(56) References Cited

OTHER PUBLICATIONS

International Preliminary Report on Patentability issued in PCT/US2016/067629; dated Jul. 5, 2018; 8 pages.
International Preliminary Report on Patentability issued in PCT/US2017/015426, dated Aug. 9, 2018, 8 pages.

* cited by examiner

FORCE SENSING CATHETER WITH IMPEDANCE-GUIDED ORIENTATION

CROSS-REFERENCE TO RELATED APPLICATION

This application claims priority to Provisional Application No. 62/288,434, filed Jan. 29, 2016, which is herein incorporated by reference in its entirety.

TECHNICAL FIELD

The present disclosure relates to medical devices and methods for ablating and/or mapping an anatomical space within a patient's body. More specifically, the disclosure relates to devices and methods for measuring a contact force on a catheter.

BACKGROUND

In ablation therapy, it may be useful to assess the contact between the ablation element and the tissue targeted for ablation. In interventional cardiac electrophysiology (EP) procedures, for example, the contact can be used to assess the effectiveness of the ablation therapy being delivered. Other catheter-based therapies and diagnostics, such as mapping, can be aided by knowing whether a part of the catheter contacts targeted tissue and to what degree the part of the catheter presses on the targeted tissue. The tissue exerts a force back on the catheter, which can be measured to assess the contact and the degree to which the catheter presses on the targeted tissue.

The present disclosure concerns, amongst other things, systems for measuring a force with a catheter.

SUMMARY

Example 1 is a catheter adapted to determine a contact force, the catheter including a proximal segment, a distal segment, and an elastic segment extending from the proximal segment to the distal segment. The distal segment includes a plurality of tip electrodes including at least three radial electrodes disposed about a circumference of the distal segment. The radial electrodes are configured to output electrical signals indicative of a contact vector of the contact force. The elastic segment includes a force sensing device configured to output an electrical signal indicative of a magnitude of an axial component of the contact force, wherein the contact force is determined by scaling the magnitude of the axial component of the contact force by the contact vector.

In example 2, the catheter of example 1, wherein the plurality of tip electrodes further includes at least one axial electrode disposed at a distal end of the distal segment, the axial electrode configured along with the radial electrodes to output electrical signals indicative of the contact vector of the contact force.

In example 3, the catheter of either of examples 1 or 2, wherein the force sensing device includes an elastic element having a longitudinal axis, and a position sensor disposed along the longitudinal axis of the elastic element and configured to output a signal indicative of relative axial movement between the proximal segment and the distal segment.

In example 4, the catheter of either of examples 1 or 2, wherein the force sensing device includes an elastic element made of a piezoresistive material and configured to output a change in an electrical resistance of the piezoresistive material indicative of a change in strain in the elastic element produced by a change in axial compression of the elastic element.

In example 5, the catheter of either of examples 3 or 4, wherein the elastic element is configured to mechanically support the distal segment in a base orientation with respect to the proximal segment, compress when the distal segment moves relative to the proximal segment in response to the application of the contact force, and resiliently return the distal segment to the base orientation with respect to the proximal segment once the contact force has been removed.

In example 6, the catheter of any of examples 1-5, wherein the plurality of tip electrodes are mapping electrodes.

In example 7, the catheter of any of examples 1-6, wherein the distal segment further includes an ablation element configured to deliver ablation therapy.

Example 8 a system for determining a contact force, the system including a catheter according to any of examples 1-7 and control circuitry. The control circuitry is configured to receive electrical signals from each of the plurality of tip electrodes, determine individual vectors for each of the plurality of tip electrodes based on their respective electrical signals, determine the contact vector of the contact force by summing the individual vectors for each of the plurality of tip electrodes, receive electrical signals from the force sensing device, determine the magnitude of the axial component of the contact force based on the electrical signals received from the force sensing device, and determine the contact force by scaling the magnitude of the axial component of the contact force by the contact vector.

In example 9, the system of example 8, wherein the individual vectors for each of the plurality of tip electrodes includes a magnitude and a direction for a corresponding tip electrode.

In example 10, the system of either of examples 8 or 9, wherein the control circuitry is further configured to cause at least one of the plurality of tip electrodes to provide a current external to the distal segment, and the magnitude of each of the individual vectors includes a voltage.

In example 11, the system of any of examples 8-10, further including a user interface having a display, wherein the control circuitry is further configured to graphically indicate on the display the magnitude and the direction of the contact force.

Example 12 is a method of determining a contact force exerted on a catheter having an elastic segment disposed between proximal and distal segments, the distal segment including a plurality of electrodes and the elastic segment including an axial force sensing device. The method includes receiving electrical signals from each of the plurality of electrodes, determining individual vectors for each of the plurality of electrodes based on their respective electrical signals, determining a contact vector of the contact force by summing the individual vectors for each of the plurality of electrodes, receiving electrical signals from the axial force sensing device, determining the magnitude of an axial component of the contact force based on the electrical signals received from the axial force sensing device, and determining the contact force by scaling the magnitude of the axial component of the contact force by the contact vector.

In example 13, the method of example 12, wherein determining the individual vectors for each of the plurality of electrodes includes determining a magnitude and a direction for a corresponding electrode.

In example 14, the method of example 13, further including causing at least one of the plurality of electrodes to provide a current external to the distal segment, wherein the magnitude determined for each of the individual vectors includes a voltage.

In example 15, the method of any of examples 12-14, further including causing a display device to present a representation of the catheter and the contact force.

Example 16 is a catheter adapted to determine a contact force, the catheter including a proximal segment, a distal segment, and an elastic segment extending from the proximal segment to the distal segment. The distal segment includes a plurality of tip electrodes including at least three radial electrodes disposed about a circumference of the distal segment. The radial electrodes are configured to output electrical signals indicative of a contact vector of the contact force. The elastic segment is configured to permit relative movement between the distal segment and the proximal segment in response to an application of the contact force on the distal segment. The elastic segment includes a force sensing device configured to output an electrical signal indicative of a magnitude of an axial component of the contact force, wherein the contact force is determined by scaling the magnitude of the axial component of the contact force by the contact vector.

In example 17, the catheter of example 16, wherein the plurality of tip electrodes further includes at least one axial electrode disposed at a distal end of the distal segment, the axial electrode configured along with the radial electrodes to output electrical signals indicative of the contact vector of the contact force.

In example 18, the catheter of example 16, wherein the force sensing device includes an elastic element having a longitudinal axis, the elastic element configured to mechanically support the distal segment in a base orientation with respect to the proximal segment, compress when the distal segment moves relative to the proximal segment in response to the application of the contact force, and resiliently return the distal segment to the base orientation with respect to the proximal segment once the contact force has been removed.

In example 19, the catheter of example 18, wherein the force sensing device further includes a position sensor disposed along the longitudinal axis of the elastic element and configured to output a signal indicative of relative axial movement between the proximal segment and the distal segment.

In example 20, the catheter of example 18, wherein the elastic element is formed of piezoresistive material and is configured to output a change in an electrical resistance of the piezo resistive material indicative of a change in strain in the elastic element produced by a change in axial compression of the elastic element.

In example 21, the catheter of example 16, wherein the plurality of tip electrodes are mapping electrodes.

In example 22, the catheter of example 16, wherein the distal segment further includes an ablation element configured to deliver ablation therapy.

Example 23 is a system for determining a contact force, the system including a catheter and control circuitry. The a catheter includes a proximal segment, a distal segment, and an elastic segment extending from the proximal segment to the distal segment. The distal segment includes a plurality of tip electrodes including at least three radial electrodes disposed about a circumference of the distal segment. The radial electrodes configured to output electrical signals indicative of a contact vector of the contact force. The elastic segment includes a force sensing device configured to output an electrical signal indicative of a magnitude of an axial component of the contact force. The control circuitry is configured to receive electrical signals from each of the plurality of tip electrodes, determine individual vectors for each of the plurality of tip electrodes based on their respective electrical signals, determine the contact vector of the contact force by summing the individual vectors for each of the plurality of tip electrodes, receive electrical signals from the force sensing device, determine the magnitude of the axial component of the contact force based on the electrical signals received from the force sensing device, and determine the contact force by scaling the magnitude of the axial component of the contact force by the contact vector.

In example 24, the system of example 23, wherein the plurality of tip electrodes further includes at least one axial electrode disposed at a distal end of the distal segment, the axial electrode configured along with the radial electrodes to output electrical signals indicative of the contact vector of the contact force.

In example 25, the system of example 23, wherein the force sensing device includes an elastic element having a longitudinal axis, the elastic element configured to mechanically support the distal segment in a base orientation with respect to the proximal segment, compress when the distal segment moves relative to the proximal segment in response to the application of the contact force, and resiliently return the distal segment to the base orientation with respect to the proximal segment once the contact force has been removed.

In example 26, the system of example 25, wherein the force sensing device further includes a position sensor disposed along the longitudinal axis of the elastic element and configured to output a signal indicative of relative axial movement between the proximal segment and the distal segment.

In example 27, the system of example 25, wherein the elastic element is formed of piezoresistive material and is configured to output a change in an electrical resistance of the piezo resistive material indicative of a change in strain in the elastic element produced by a change in axial compression of the elastic element.

In example 28, the system of example 23, wherein the individual vectors for each of the plurality of tip electrodes includes a magnitude and a direction for a corresponding tip electrode.

In example 29, the system of example 23, wherein the control circuitry is further configured to cause at least one of the plurality of tip electrodes to provide a current external to the distal segment, and the magnitude of each of the individual vectors includes a voltage.

In example 30, the system of example 23, further including a user interface having a display, wherein the control circuitry is further configured to graphically indicate on the display the magnitude and the direction of the contact force.

Example 31 is a method of determining a contact force exerted on a catheter having an elastic segment disposed between proximal and distal segments, the distal segment including a plurality of mapping electrodes and the elastic segment including an axial force sensing device. The method includes receiving electrical signals from each of the plurality of mapping electrodes, determining individual vectors for each of the plurality of mapping electrodes based on their respective electrical signals, determining a contact vector of the contact force by summing the individual vectors for each of the plurality of mapping electrodes, receiving electrical signals from the axial force sensing device, determining the magnitude of an axial component of the contact force based on the electrical signals received from the axial force sensing device, and determining the contact force by scaling the magnitude of the axial component of the contact force by the contact vector.

In example 32, the method of example 31, wherein determining the individual vectors for each of the plurality of mapping electrodes includes determining a magnitude and a direction for a corresponding mapping electrode.

In example 33, the method of example 31, further including causing at least one of the plurality of mapping electrodes to provide a current external to the distal segment, wherein the magnitude determined for each of the individual vectors includes a voltage.

In example 34, the method of any of examples 31, further including causing a display device to present a representation of the catheter and the contact force.

In example 35, the method of any of examples 31, further including filtering the received electrical signals from each of the plurality of mapping electrodes to remove electrical signals from an ablation procedure.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1A:
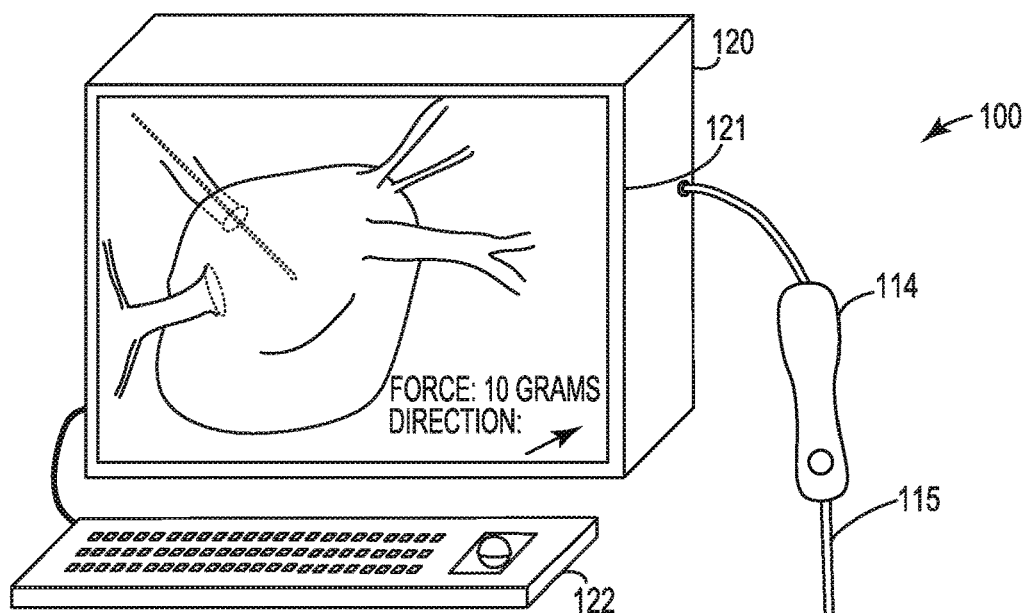
FIGS. 1A-1C show a system for measuring a force with a catheter in accordance with various embodiments of this disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various cardiac abnormalities can be attributed to improper electrical activity of cardiac tissue. Such improper electrical activity can include, but is not limited to, generation of electrical signals, conduction of electrical signals, and/or mechanical contraction of the tissue in a manner that does not support efficient and/or effective cardiac function. For example, an area of cardiac tissue may become electrically active prematurely or otherwise out of synchrony during the cardiac cycle, thereby causing the cardiac cells of the area and/or adjacent areas to contract out of rhythm. The result is an abnormal cardiac contraction that is not timed for optimal cardiac output. In some cases, an area of cardiac tissue may provide a faulty electrical pathway (e.g., a short circuit) that causes an arrhythmia, such as atrial fibrillation or supraventricular tachycardia. In some cases, inactivate tissue (e.g., scar tissue) may be preferable to malfunctioning cardiac tissue.

Cardiac ablation is a procedure by which cardiac tissue is treated to inactivate the tissue. The tissue targeted for ablation may be associated with improper electrical activity, as described above. Cardiac ablation can lesion the tissue and prevent the tissue from improperly generating or conducting electrical signals. For example, a line, a circle, or other formation of lesioned cardiac tissue can block the propagation of errant electrical signals. In some cases, cardiac ablation is intended to cause the death of cardiac tissue and to have scar tissue reform over the lesion, where the scar tissue is not associated with the improper electrical activity. Lesioning therapies include electrical ablation, radiofrequency ablation, cyroablation, microwave ablation, laser ablation, and surgical ablation, among others. While cardiac ablation therapy is referenced herein as an exemplar, various embodiments of the present disclosure can be directed to ablation of other types of tissue and/or to non-ablation diagnostic and/or catheters that deliver other therapies.

Ideally, an ablation therapy can be delivered in a minimally invasive manner, such as with a catheter introduced to the heart through a vessel, rather than surgically opening the heart for direct access (e.g., as in a maze surgical procedure). For example, a single catheter can be used to perform an electrophysiology study, also known as mapping, of the inner surfaces of a heart to identify electrical activation patterns. From these patterns, a clinician can identify areas of inappropriate electrical activity and ablate cardiac tissue in a manner to kill or isolate the tissue associated with the inappropriate electrical activation. However, the lack of direct access in a catheter-based procedure may require that the clinician only interact with the cardiac tissue through a single catheter and keep track of all of the information that the catheter collects or is otherwise associated with the procedure. In particular, it can be challenging to determine the location of the therapy element (e.g., the proximity to tissue), the quality of a lesion, and whether the tissue is fully lesioned, under-lesioned (e.g., still capable of generating and/or conducting unwanted electrical signals), or over-lesioned (e.g., burning through or otherwise weakening the cardiac wall). The quality of the lesion can depend on the degree of contact between the ablation element and the targeted tissue. For example, an ablation element that is barely contacting tissue may not be adequately positioned to deliver effective ablation therapy. Conversely, an ablation element that is pressed too hard into tissue may cause a perforation.

The present disclosure concerns, among other things, methods, devices, and systems for assessing a degree of contact between a part of a catheter (e.g., an ablation element) and tissue. Knowing the degree of contact, such as the magnitude and the direction of a force generated by contact between the catheter and the tissue, can be useful in determining the degree of lesioning of the targeted tissue. Information regarding the degree of lesioning of cardiac tissue can be used to determine whether the tissue should be further lesioned or whether the tissue was successfully ablated, among other things. Additionally or alternatively, an indicator of contact can be useful when navigating the catheter because a user may not feel a force being exerted on the catheter from tissue as the catheter is advanced within a patient, thereby causing vascular or cardiac tissue damage or perforation.

Figure 1B:
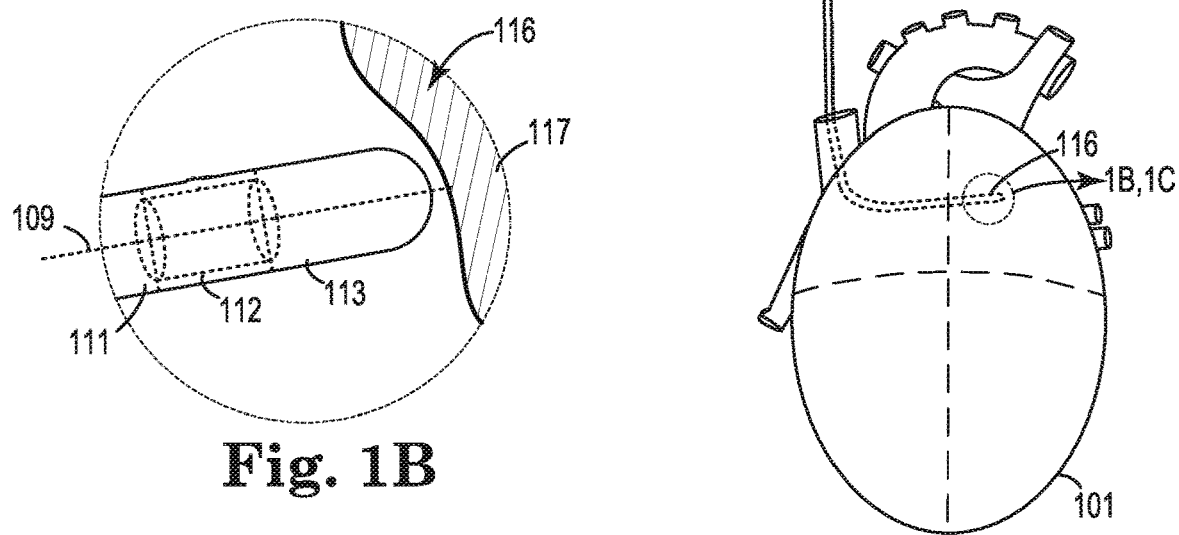
Figure 1C:
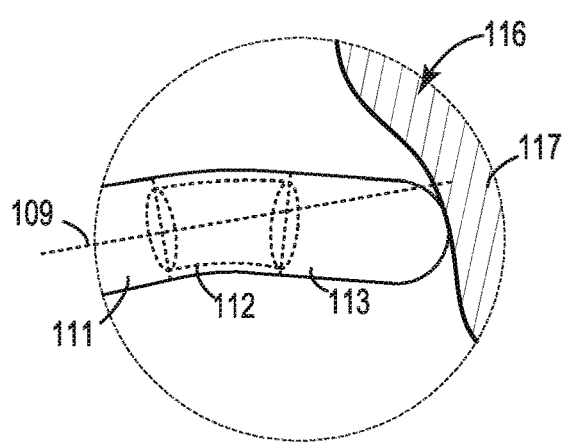

FIGS. 1A-1C illustrate an embodiment of a system 100 for sensing data from inside the body and/or delivering therapy. For example, the system 100 can be configured to map cardiac tissue and/or ablate the cardiac tissue, among other options. The system 100 includes a catheter 110 connected to a control unit 120 via handle 114. The catheter 110 can comprise an elongated tubular member having a proximal end 115 connected with the handle 114 and a distal end 116 configured to be introduced within a heart 101 or other area of the body. As shown in FIG. 1A, the distal end 116 of the catheter 110 is within the left atrium.

As shown in FIG. 1B, the distal end 116 of the catheter 110 includes a proximal segment 111, an elastic segment 112, and a distal segment 113. The proximal segment 111, the elastic segment 112, and the distal segment 113 can be coaxially aligned with each other in a base orientation as shown in FIG. 1B. Specifically, each of the proximal segment 111, the elastic segment 112, and the distal segment 113 are coaxially aligned with a common longitudinal axis 109. The longitudinal axis 109 can extend through the radial center of each of the proximal segment 111, the elastic segment 112, and the distal segment 113, and can extend through the radial center of the distal end 116 as a whole. The proximal segment 111, the elastic segment 112, and the distal segment 113 can be mechanically biased to assume the base orientation. In some embodiments, the coaxial alignment of the proximal segment 111 with the distal segment 113 can correspond to the base orientation. As shown, the distal end 116, at least along the proximal segment 111, the elastic segment 112, and the distal segment 113, extends straight. In some embodiments, this straight arrangement of the proximal segment 111, the elastic segment 112, and the distal segment 113 can correspond to the base orientation.

The distal segment 113 includes a plurality of tip electrodes configured to sense local impedance changes to determine a contact vector, as further discussed herein. In other embodiments, the plurality of tip electrodes can additionally be configured for sensing electrical activity, such as electrical cardiac signals, and may be known as mapping electrodes. In other embodiments, the distal segment 113 can additionally or alternatively include an ablation electrode to be used to deliver ablative energy to tissue.

The catheter 110 includes force sensing capabilities. For example, as shown in FIGS. 1B and 1C, the catheter 110 is configured to sense a force due to engagement with tissue 117 of heart 101. The distal segment 113 can be relatively rigid while segments proximal of the distal segment 113 can be relatively flexible. In particular, the elastic segment 112 may be more flexible than the distal segment 113 and the proximal segment 111 such that when the distal end 116 of the catheter 110 engages tissue 117, the elastic segment 112 bends and compresses, as shown in FIG. 1C. For example, the distal end 116 of the catheter 110 can be generally straight as shown in FIG. 1B. When the distal segment 113 engages tissue 117, the distal end 116 of the catheter 110 can bend and compress at the elastic segment 112 such that the distal segment 113 moves relative to the proximal segment 111. As shown in FIGS. 1B and 1C, the normal force from the tissue moves the distal segment 113 out of coaxial alignment (e.g., with respect to the longitudinal axis 109) with the proximal segment 111 causing the elastic segment 112 to compress. As such, proximal segment 111 and the distal segment 113 may be axially incompressible to not compress due to the force while the elastic segment 112 may be less stiff and compress to accommodate the force exerted on the distal end 116 of the catheter 110. A force sensing device within the distal end 116 of the catheter 110 can sense the degree of axial compression of the elastic segment 112 for use in determining the magnitude and the direction of the contact force by scaling the axial component of the magnitude of the contact force by the contact vector, as further discussed herein.

The control unit 120 of the system 100 includes a display 121 (e.g., a liquid crystal display or a cathode ray tube) for displaying information. The control unit 120 further includes a user input 122 which can include one or more buttons, toggles, a track ball, a mouse, touchpad, or the like for receiving user input. The user input 122 can additionally or alternatively be located on the handle 114. The control unit 120 can contain control circuitry for performing the functions referenced herein. Some or all of the control circuitry can alternatively be located within the handle 114.

Figure 2:
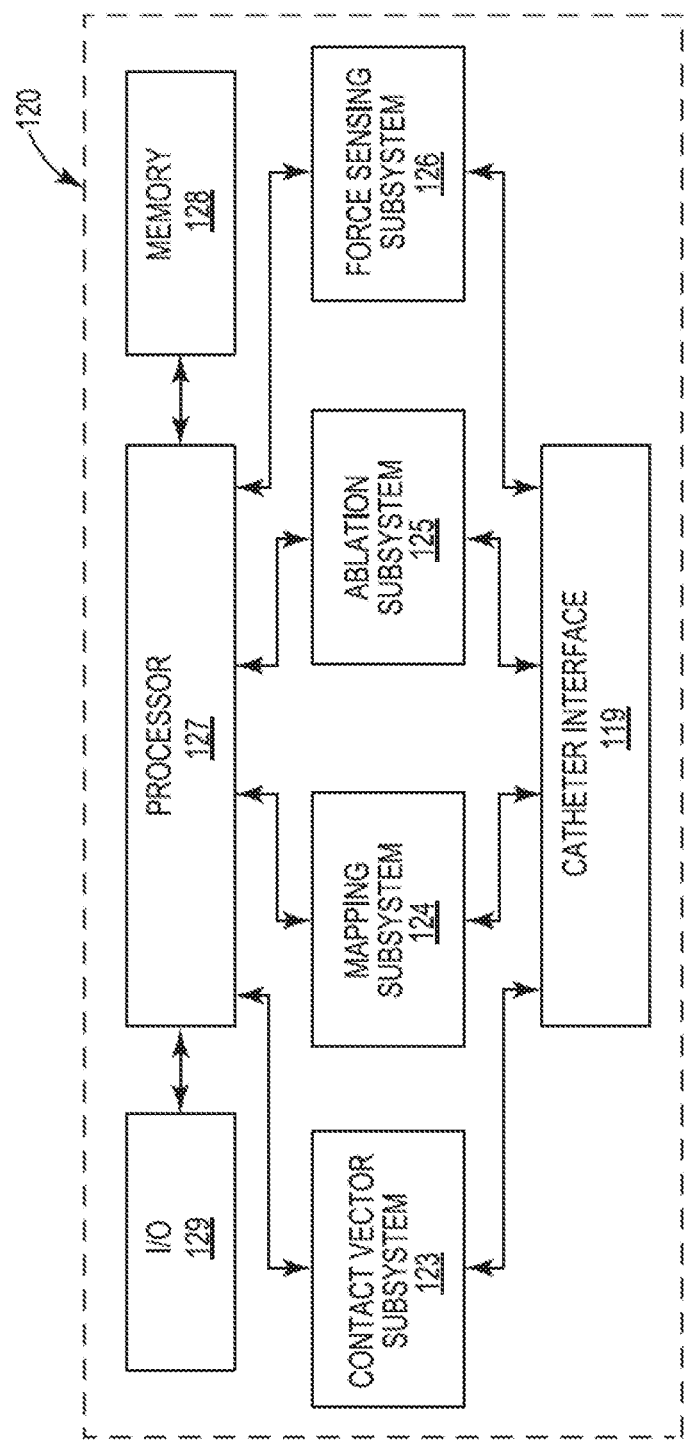
FIG. 2 shows a block diagram of circuitry for controlling various functions described herein.

FIG. 2 illustrates a block diagram showing an example of control circuitry which can perform functions referenced herein. This or other control circuitry can be housed within control unit 120, which can comprise a single housing or multiple housings among which components are distributed. Control circuitry can additionally or alternatively be housed within the handle 114. The components of the control unit 120 can be powered by a power supply (not shown), as known in the art, which can supply electrical power to any of the components of the control unit 120 and the system 100. The power supply can plug into an electrical outlet and/or provide power from a battery, among other options.

The control unit 120 can include a catheter interface 119. The catheter interface 119 can include a plug which receives a cord from the handle 114. The catheter 110 can include multiple conductors (not illustrated but known in the art) to convey electrical signals between the distal end 116 and the proximal end 115 and further to the catheter interface 119. It is through the catheter interface 119 that the control unit 120 (and/or the handle 114 if control circuitry is included in the handle 114) can send electrical signals to any element within the catheter 110 and/or receive an electrical signal from any element within the catheter 110. The catheter interface 119 can conduct signals to any of the components of the control unit 120.

The control unit 120 can include a contact vector subsystem 123. The contact vector subsystem 123 can include components for operating the contact vector determining functions of the system 100. Such components can include a high-frequency sub-threshold current generator and multiplexor configured to selectively deliver energy to the plurality of tip electrodes for determining tissue impedance, as well as signal processing circuitry configured to filter and process electrical signals from the tip electrodes for determining a contact vector, as further discussed herein. The sub-threshold energy is at a current that is below an ablation delivery energy or an energy needed to stimulate cardiac muscle. Providing sub-threshold energy to tip electrodes for determining tissue impedance is further described in U.S. Provisional Patent Application No. 62/258,396 incorporated herein by reference in its entirety for all purposes. The contact vector subsystem 123 can send signals to elements within the catheter 110 via the catheter interface 119 and/or receive signals from elements within the catheter 110 via the catheter interface 119.

The control unit 120 can include a mapping subsystem 124. The mapping subsystem 124 can include components for operating the mapping functions of the system 100. While the illustrated example of control circuitry shown in FIG. 2 includes the mapping subsystem, it will be understood that not all embodiments may include mapping subsystem 124 or any circuitry for mapping cardiac tissue. The mapping subsystem 124 can include signal processing circuitry configured to filter and process electrical signals from the tip electrodes to detect localized intra cardiac electrical activity. In some embodiments, the catheter 110 may be a configured to be used for both localized mapping and ablation functions, providing localized, high resolution ECG signals during an ablation procedure. In such embodiments, the signal processing circuitry of the mapping subsystem 124 can be configured to filter the electrical signals (i.e., local electrograms or impedance measurements) received from the tip electrodes to remove noise introduced from ablation energy. The mapping subsystem 124 can receive signals from elements within the catheter 110 via the catheter interface 119.

The control unit 120 can include an ablation subsystem 125. The ablation subsystem 125 can include components for operating the ablation functions of the system 100. While the illustrated example of control circuitry shown in FIG. 2 includes the ablation subsystem, it will be understood that not all embodiments may include ablation subsystem 125 or any circuitry for generating an ablation therapy. The ablation subsystem 125 can include an ablation generator to provide different therapeutic outputs depending on the particular configuration (e.g., a high frequency alternating current signal in the case of radiofrequency ablation to be output through one or more electrodes). Providing ablation energy to target sites is further described, for example, in U.S. Pat. Nos. 5,383,874 and 7,720,420, each of which is expressly incorporated herein by reference in its entirety for all purposes. The ablation subsystem 125 may support any other type of ablation therapy, such as microwave ablation. The ablation subsystem 125 can deliver signals or other type of ablation energy through the catheter interface 119 to the catheter 110.

The control unit 120 can include a force sensing subsystem 126. The force sensing subsystem 126 can include components for measuring an axial force experienced by the catheter 110. Such components can include signal processors, analog-to-digital converters, operational amplifiers, comparators, and/or any other circuitry for conditioning and measuring one or more signals. The force sensing subsystem 126 can send signals to elements within the catheter 110 via the catheter interface 119 and/or receive signals from elements within the catheter 110 via the catheter interface 119.

Each of the contact vector subsystem 123, the mapping subsystem 124, the ablation subsystem 125, and the force sensing subsystem 126 can send signals to, and receive signals from, the processor 127. The processor 127 can be any type of processor for executing computer functions. For example, the processor 127 can execute program instructions stored within the memory 128 to carry out any function referenced herein, such as determining a magnitude and direction of a force experienced by the catheter 110.

The control unit 120 further includes an input/output subsystem 129 which can support user input and output functionality. For example, the input/output subsystem 129 may support the display 121 to display any information referenced herein, such as a graphic representation of tissue, the catheter 110, and a magnitude and direction of the force experienced by the catheter 110, amongst other options. Input/output subsystem 129 can log key and/or other input entries via the user input 122 and route the entries to other circuitry.

A single processor 127, or multiple processors, can perform the functions of one or more subsystems, and as such the subsystems may share control circuitry. Although different subsystems are presented herein, circuitry may be divided between a greater or lesser numbers of subsystems, which may be housed separately or together. In various embodiments, circuitry is not distributed between subsystems, but rather is provided as a unified computing system. Whether distributed or unified, the components can be electrically connected to coordinate and share resources to carry out functions.

Figure 3:
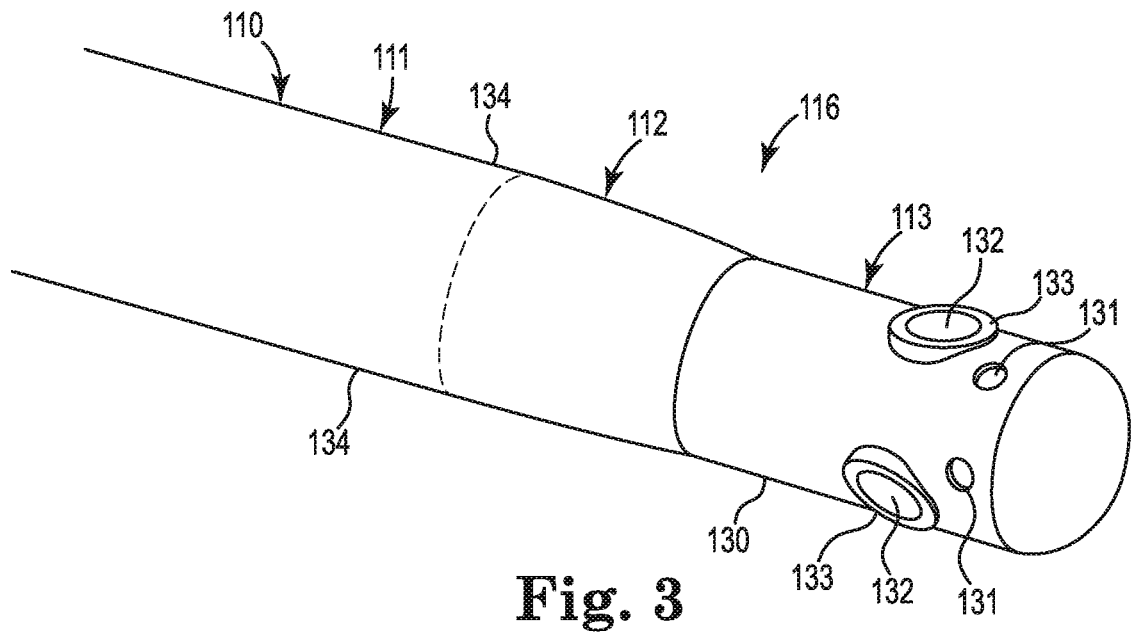
FIG. 3 shows a perspective view of a distal end of a catheter in accordance with various embodiments of this disclosure.

FIG. 3 illustrates a detailed view of the distal end 116 of the catheter 110. As shown, the proximal segment 111 can be proximal and adjacent to the elastic segment 112. The elastic segment 112 is adjacent to the distal segment 113.

As shown in FIG. 3, the catheter 110 is an ablation catheter and the distal segment 113 can include an ablation electrode 130, a plurality of ports 131, and a plurality of tip electrodes 132. The ablation electrode 130 can be in a shell form which largely defines the distal segment 113, and can contain other components. In other embodiments, the distal segment 113 may not include, and may not be defined by, the ablation electrode 130. In some embodiments, the plurality of ports 131 may be fluidly connected to a source of irrigation fluid for flushing the exterior volume adjacent to the distal segment 113. The tip electrodes 132 can be mini-electrodes which may each be about 1 millimeter in diameter and can be equally distributed about the circumference of the distal segment 113, as shown more clearly in FIGS. 6 and 8. Each of the tip electrodes 132 can be electrically isolated from the ablation electrode 130 by an insulator 133. Although the embodiment of FIG. 3 has three tip electrodes 132 (two visible in FIG. 3) equally disposed about 120 degrees from each other about the circumference of the distal segment 113, it is understood that other embodiments may have more than three tip electrodes 132 distributed about the circumference of the distal segment 113 and/or that the tip electrodes 132 may not be equally distributed about the circumference of the distal segment so long as the relative locations of the tip electrodes 132 are known.

As further shown in FIG. 3, the catheter 110 includes a catheter shaft 134. The catheter shaft 134 can extend from the distal segment 113 to the handle 114 (FIG. 1A), and thus define an exterior surface of the catheter 110 along the elastic segment 112, the proximal segment 111, and further proximally to the proximal end 115 (FIG. 1A). The catheter shaft 134 can be a tube formed from various polymers, such as polyurethane, nylon-family polymers, polyamide, polyether block amide, silicone, and/or other materials. In some embodiments, the catheter shaft 134 may be relatively flexible, and at least along the elastic segment 112 may not provide any material mechanical support to the distal segment 113 (e.g., facilitated by thinning of the wall of the catheter shaft 134 along the elastic segment 112).

Figure 4:
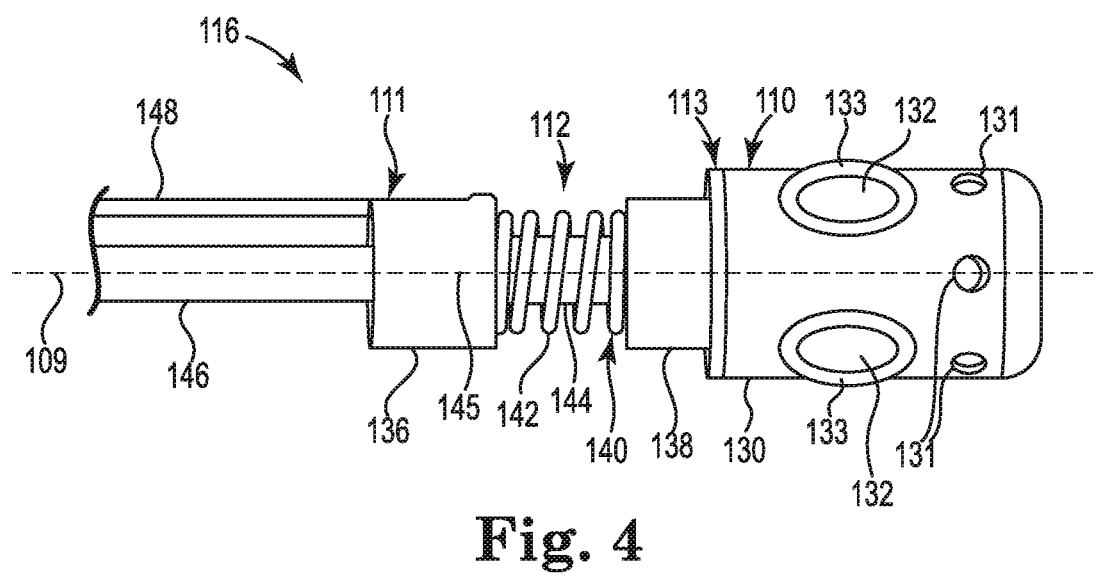
FIG. 4 shows a side view of the inside of the distal end of the catheter of FIG. 3 in accordance with various embodiments of this disclosure.

FIG. 4 shows a side view of the inside of the distal end 116 of the catheter 110 of FIG. 3 after the removal of the catheter shaft 134 to expose various components that underlie the catheter shaft 134. As shown in FIG. 4, the proximal segment 111 may include a proximal ring 136, the distal segment 113 may include a distal ring 138, and the elastic segment 112 may include a force sensing device 140. One or both of the proximal ring 136 and the distal ring 138 can be formed from polymer materials, such as polyethylene, or PEEK, or can be formed from a metal, such as stainless steel. One or both of the proximal ring 136 and the distal ring 138 can be formed from a composite of metal, polymer, and/or other materials. The force sensing device 140 can be attached on proximal and distal ends to the proximal ring 136 and the distal ring 138, respectively.

In the embodiment of FIG. 4, the force sensing device 140 can include an elastic element 142 and a position sensor 144. The elastic element 142 has a longitudinal axis 145. The elastic element 142 is depicted as a coiled spring, but may have other suitable forms as are known in the art. The elastic element 142 can be formed from a resilient material, for example, polymer materials, metals (e.g. stainless steel, nitinol), or other materials. In some embodiments, the elastic element 142 may be formed from a stainless steel hypotube. The elastic element 142 is attached to the proximal ring 136 and the distal ring 138 and has a longitudinal axis 145. The position sensor 144 is disposed along the longitudinal axis 145 of the elastic element 142. The position sensor 144 can be, for example, a mini inductive position sensor, a linear variable differential transformer (LVDT), a capacitive sensor, an optical sensor, an ultrasonic sensor, or a strain gauge sensor. The position sensor 144 can also be attached to the proximal ring 136 and the distal ring 138. Alternatively, the position sensor 144 can be attached on its distal end to any structure within the distal segment 113, and can be attached on its proximal end to any structure within the proximal segment 112. In any case, the position sensor 144 is configured to output a signal indicative of relative axial movement between the proximal segment 111 and the distal segment 113, as discussed below.

In the base orientation, the proximal ring 136, the distal ring 138, and the force sensing device 140 can be coaxially aligned with respect to the longitudinal axis 109, as shown in FIG. 4. For example, the longitudinal axis 109 can extend through the respective radial centers of each of the proximal ring 136, the distal ring 138, and the force sensing device 140. An inner tube 146 can extend through the catheter 110 (e.g., from the handle 114, FIG. 1A), to the proximal ring 136, and can include one or more lumens within which one or more conductors (not illustrated) can extend from the proximal end 115 (FIG. 1A) to the distal segment 113, such as for connecting with one or more electrical elements (e.g., tip electrodes 132, ablation electrode 130, position sensor 144, or other components). Coolant fluid can additionally or alternatively be routed through the inner tube 146. In various embodiments, the catheter 110 is open irrigated (e.g., through the plurality of ports 131) to allow the coolant fluid to flow out of the distal segment 113. Various other embodiments concern a non-irrigated catheter 110.

One or more tethers 148 (one shown) can attach to the proximal ring 136. Considering FIGS. 1A and 4, together, the tether 148 can attach to a deflection mechanism within the handle 114 to cause deflection of the distal end 116. A knob, slider, or plunger on a handle 114 may be used to create tension or slack in the tether 148.

As shown in FIG. 4, the elastic segment 112 can extend from a distal edge of the proximal ring 136 to a proximal edge of the distal ring 138. As such, the proximal ring 136 can be part of, and may even define the length of, the proximal segment 111 (FIG. 1A). Likewise, the distal ring 138 can be part of the distal segment 113. The elastic segment 112 can be a relatively flexible portion that is mostly or entirely mechanically supported by the elastic element 142. As such, the proximal ring 136 and the distal ring 138 can be stiffer than the elastic element 142 such that a contact force directed on the distal segment 113 causes the distal end 116 to bend along the elastic element 142 rather than along the distal segment 113 or the proximal segment 111.

Thus, the elastic element 142 can allow the distal segment 113 to move relative to the proximal segment 111 based on the contact force exerted on the distal segment 113, and can resiliently return the distal segment 113 to its original orientation with respect to the proximal segment 111 once the contact force has been removed. As the elastic element 142 compresses during the exertion of the contact force on the distal segment, the position sensor 144 outputs a signal indicative of relative axial movement between the proximal segment 111 and the distal segment 113 against the restoring force of the elastic element 142. The force sensing subsystem 126 of the control unit 120 (FIG. 2) can use this electrical signal to determine a magnitude of an axial component of the contact force. The magnitude of the axial component of the contact force can be calculated using Hooke's law, wherein the displacement of an elastic element (e.g., elastic element 142) is proportional to the forced placed on element, based on a predetermined constant. Only the magnitude of the axial component of the contact force exerted on the distal end is determined by the force sensing subsystem 126 because there is only one position sensor 144 and it is disposed along the longitudinal axis of the elastic element 142.

In the embodiment of FIG. 4, the force sensing device 140 includes the elastic element 142 and the position sensor 144. In other embodiments, the force sensing device 140 includes only on the elastic element 142. In such embodiments, the elastic element 142 is formed of a piezoresistive material such that when strain is applied to the elastic element 142, the electrical resistivity of the elastic element 142 changes. So configured, the elastic element 142 can output a change in the electrical resistance of the piezoresistive material indicative of the change in strain in in the elastic element 142 produced by a change in axial compression of the elastic element 142. The force sensing subsystem 126 of the control unit 120 (FIG. 2) can use this electrical signal to determine a magnitude of an axial component of a contact force exerted on the distal segment 113.

Figure 5:
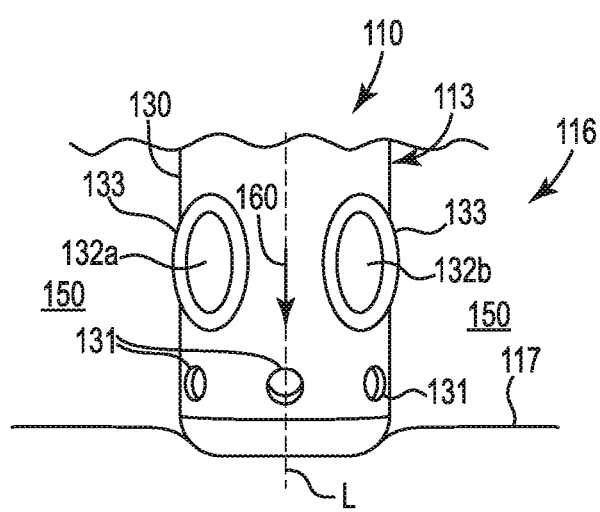
FIG. 5 shows a side view of the distal end of the catheter of FIGS. 3 and 4 in axial contact with cardiac tissue.
Figure 6:
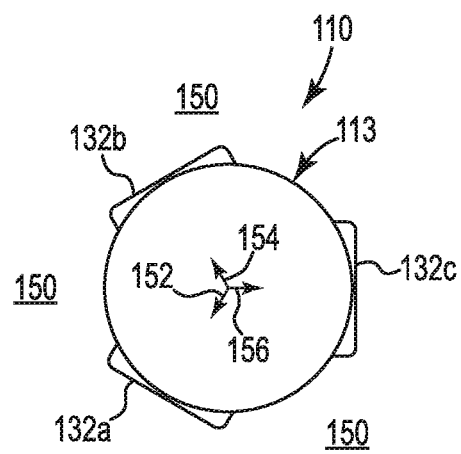
FIG. 6 shows a schematic end view of the catheter of FIG. 5.

FIG. 5 shows a side view of the distal end 116 of the catheter 110 of FIGS. 3 and 4 largely surrounded by a blood pool 150 and in axial contact with tissue 117 of heart 101 (FIG. 1A). FIG. 6 shows schematic end view of the catheter 110 of FIG. 5. Considering FIGS. 5 and 6 together, the plurality of tip electrodes 132 are specifically designated radial electrodes 132a, 132b, and 132c as each faces a radial direction with respect to a longitudinal axis L of the distal segment 113. A current driven through any of the tip electrodes 132 (or in some embodiments, the ablation electrode 130) produces voltages which may be sensed by the tip electrodes 132 and output as electrical signals. That is, the driven current produces voltages sensed at each of the radial electrodes 132*a*, 132*b*, or 132*c*, by the contact vector subsystem 123. The voltages may be represented as individual vectors 152, 154, and 156 having a magnitude of the sensed voltage and a direction extending radially outward toward the radial electrodes 132*a*, 132*b*, or 132*c*, respectively, from a point closest to, and equidistant from, the radial electrodes 132*a*, 132*b*, or 132*c*, as shown in FIG. 6. For a given sub-threshold current, the voltages sensed at each of the radial electrodes 132*a*, 132*b*, or 132*c* are largely a function of the impedance of the external environment adjacent to each of the radial electrodes 132*a*, 132*b*, or 132*c*. Control circuitry within the control unit 120 (e.g. within contact vector subsystem 123 or processor 127) can sum the three voltage vectors 152, 154, and 156 to determine a contact vector 160.

In the example shown in FIGS. 5 and 6, the radial electrodes 132*a*, 132*b*, or 132*c* experience the same external environment—the blood pool 150, so the three voltages may be equal. The control circuitry sums the voltage vectors 152, 154, and 156 to determine a contact vector 160 having zero magnitude and an undetermined direction. Taken alone, the contact vector 160 may mean either axial contact, or no contact at all. The control circuitry combines the contact vector 160 with the magnitude of an axial component of a contact force determined by force sensing subsystem 126 to determine that the contact vector 160 is in the axial direction. Since the contact vector 160 is in the axial direction, the control circuitry determines the contact force by scaling the axial component of the magnitude of the contact force at 1:1. That is, the magnitude of an axial component of the contact force determined by force sensing subsystem 126 is a direct measurement of the magnitude of the contact force.

Figure 7:
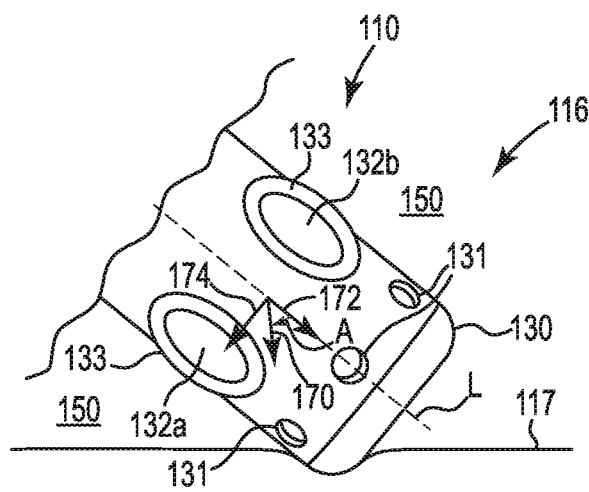
FIG. 7 shows a side view of the distal end of the catheter of FIGS. 3 and 4 in angled contact with cardiac tissue.
Figure 8:
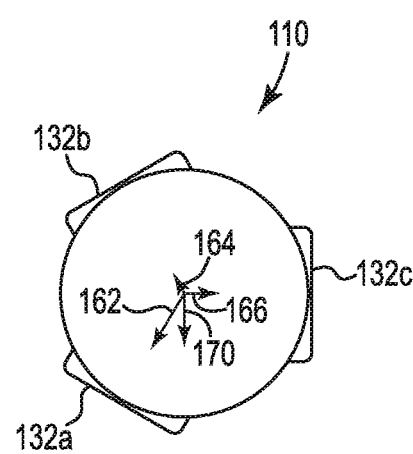
FIG. 8 shows a schematic end view of the catheter of FIG. 7.

FIG. 7 shows a side view of the distal end 116 of the catheter 110 of FIGS. 3 and 4 in angled contact with tissue 117 of heart 101 (FIG. 1A). FIG. 8 shows schematic end view of the catheter 110 of FIG. 7. In the example of FIGS. 7 and 8, the radial electrodes 132*a*, 132*b*, and 132*c* do not experience the same external environment. Due to the angled contact, the external environment of radial electrode 132*a* includes more of the tissue 117 and less of the blood pool 150 than either of the other radial electrodes 132*b* or 132*c*. Cardiac tissue, such as tissue 117, has a higher impedance than blood, as is known in the art. As a result, the magnitude of the sensed voltage at the radial electrode 132*a* may be higher than the magnitudes of the voltages either of the radial electrodes 132*b* or 132*c*. Similarly, the external environment of radial electrode 132*c* includes more of the tissue 117 and less of the blood pool 150 than the radial electrode 132*b*. Thus, the magnitude of the sensed voltage at the radial electrode 132*c* may be higher than the magnitude of the voltage of the radial electrode 132*b*. The voltages may be represented as individual vectors 162, 164, and 166 having a magnitude of the sensed voltage and a direction extending radially outward toward the radial electrodes 132*a*, 132*b*, or 132*c* from a point closest to, and equidistant from, the radial electrodes 132*a*, 132*b*, or 132*c*, as shown in FIG. 8. The control circuitry can sum the three voltage vectors 162, 164, and 166 to determine a contact vector 170, as shown in FIG. 8. The direction of contact vector 170 is the direction of the contact force.

FIG. 7 shows the contact vector 170 at an angle A to the longitudinal axis L. The angle A may be proportional to the magnitude of vector 162. That is, as the angle A increases, the radial electrode 132*a* becomes closer to the tissue 117, increasing the amount of tissue 117 in the external environment of radial electrode 132*a* and, therefore, increasing the magnitude of vector 162. In this way, the angle A may found and the contact vector 170 determined in three dimensions. Once angle A is determined, the contact vector 170 may be resolved into an axial vector component 172 and a radial vector component 174 using geometrical techniques known in the art. The magnitude of the axial vector component 172 equals the magnitude of the axial component of the contact force determined by force sensing subsystem 126. Geometrical techniques known in the art may be used to scale the axial component of the contact force by the contact vector 170 to determine the magnitude of the contact force.

Figure 9:
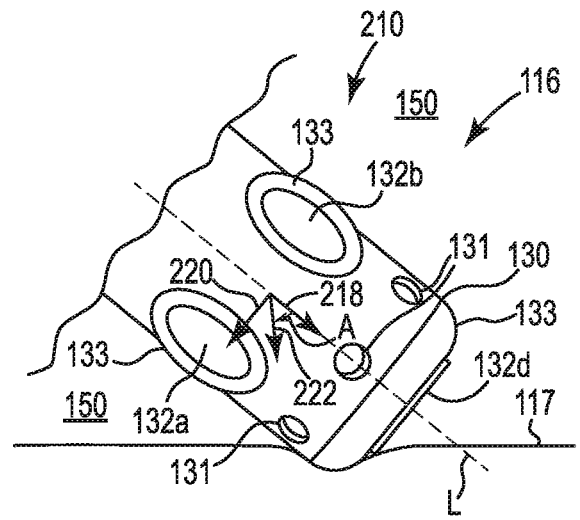
FIG. 9 shows a side view of the distal end of another embodiment of a catheter in accordance with various embodiments of this disclosure.
Figure 10:
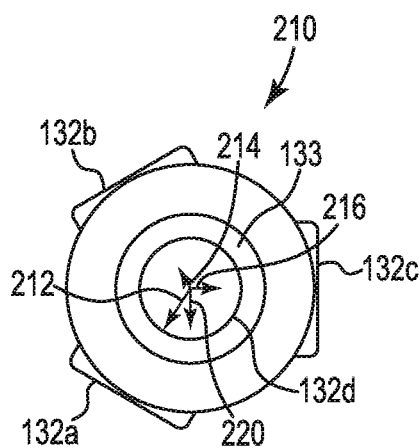
FIG. 10 shows a schematic end view of the catheter of FIG. 9.

FIGS. 9 and 10 illustrate another embodiment of a catheter in accordance with various embodiments of this disclosure. FIG. 9 shows a side view of the distal end of catheter 210 in angled contact with the cardiac tissue 117. The catheter 210 is identical to catheter described above, except that catheter 210 further includes another tip electrode 132, an axial electrode 132*d*, disposed at a distal end of the distal segment 113 and facing axially outward with respect to the longitudinal axis L. As with the embodiment described above in reference to FIGS. 4-8, a current driven through any of the tip electrodes 132 (or in some embodiments, the ablation electrode 130) produces voltages which may be sensed by the tip electrodes 132 and output as electrical signals. That is, the driven current produces voltages sensed at each of the radial electrodes 132*a*, 132*b*, or 132*c*, and the axial electrode 132*d* by the contact vector subsystem 123. The voltages may be represented as individual vectors 212, 214, 216, and 218 having a magnitude of the sensed voltage and a direction extending outward toward the radial electrodes 132*a*, 132*b*, 132*c* and axial electrode 132*d* from a point closest to, and equidistant from, the radial electrodes 132*a*, 132*b*, 132*c*, and the axial electrode 132*d*, as shown in FIGS. 9 and 10. The control circuitry can sum the three voltage vectors 212, 214, and 216 to determine an intermediate vector 220, as shown in FIG. 9. The control circuitry can sum the voltage vectors 218 and 220 to determine a contact vector 222 as shown in FIG. 10. The direction of contact vector 222 is the direction of the contact force.

The contact vector 222 may be resolved into axial and radial vector components as described above in reference to FIG. 7 using geometrical techniques known in the art. The axial component of the contact force determined by force sensing subsystem 126 equals the magnitude of the axial vector component of contact vector 222. Thus, the axial component of the contact force may be scaled by the contact vector 222 to determine the magnitude of the contact force.

Figure 11:
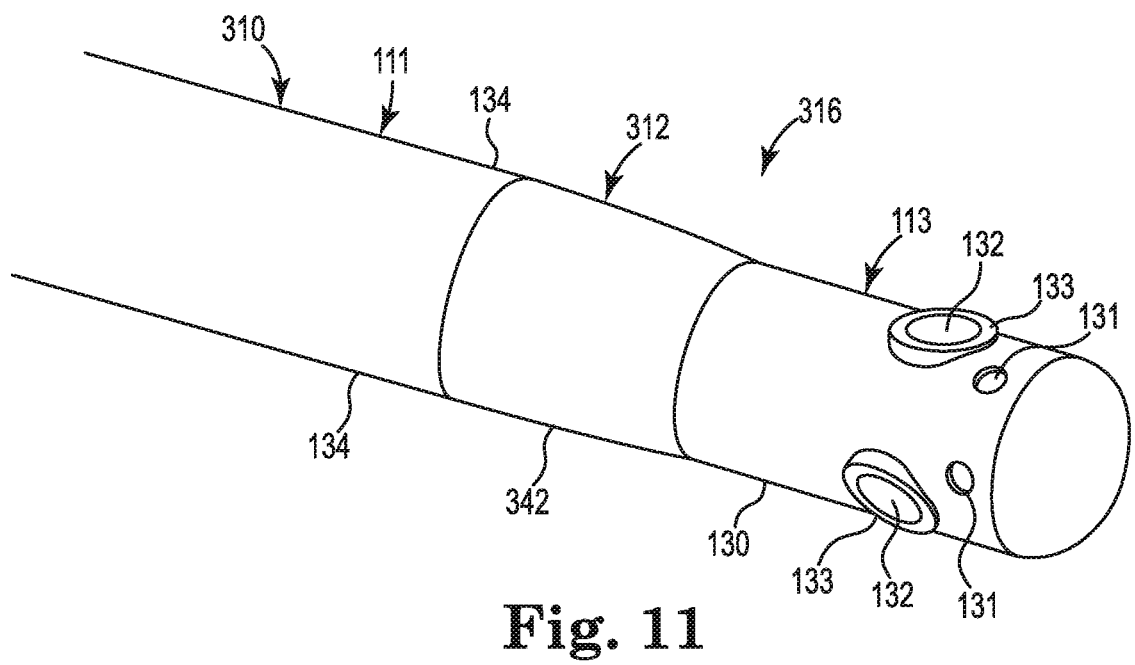
FIG. 11 shows a perspective view of a distal end of another embodiment of a catheter in accordance with various embodiments of this disclosure.
Figure 12:
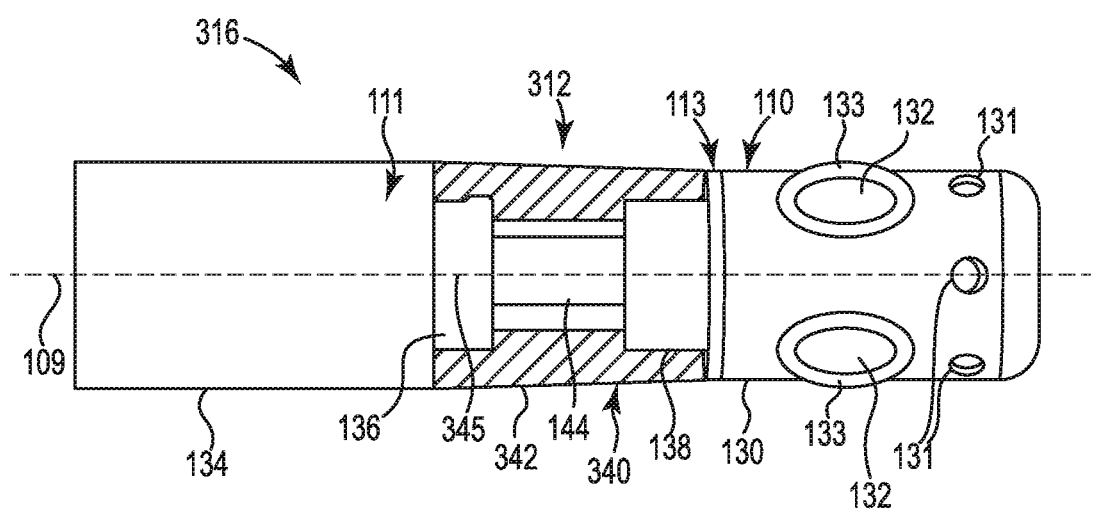
FIG. 12 shows a side view of the inside of the distal end of the catheter of FIG. 11 in accordance with various embodiments of this disclosure.

FIGS. 11 and 12 illustrate another embodiment of a catheter in accordance with various embodiments of this disclosure. FIG. 11 shows a distal end 316 of a catheter 310. The catheter 310 is identical to catheter 110 described above, except that the elastic element 142 is replaced by an elastic element 342 to form an elastic segment 312, and the catheter shaft 134 extends from the distal segment 113 to the elastic segment 312, but does define the exterior surface of catheter 310 along the elastic segment 312. That is, the elastic element 342 defines the exterior surface of catheter 310 along the elastic segment 312.

FIG. 12 shows a side view of inside of the distal end 316 of the catheter 310. As shown in FIG. 12, the elastic segment 312 includes a force sensing device 340. The force sensing device 340 includes the elastic element 342 and the position sensor 144 described above in reference to FIG. 4. The elastic element 342 is shown in cross-section for clarity. The elastic element 342 may be a biocompatible elastomeric polymer, for example, silicone rubber. The elastic element 342 has a longitudinal axis 345. The position sensor 144 is disposed along the longitudinal axis 345 of the elastic element 342. The elastic element 342 can be attached to the proximal ring 136 and to the distal ring 138 by lap joints, as shown in FIG. 12. The elastic element 342 may completely surround the position sensor 144 without contacting the position sensor 144, as shown.

As with the elastic element 142 described above, the elastic element 342 can allow the distal segment 113 to move relative to the proximal segment 111 based on the contact force exerted on the distal segment 113, and can resiliently return the distal segment 113 to its original orientation with respect to the proximal segment 111 once the contact force has been removed. As the elastic element 342 compresses during the exertion of the contact force on the distal segment, the position sensor 144 outputs a signal indicative of relative axial movement between the proximal segment 111 and the distal segment 113 against the restoring force of the elastic element 342. The force sensing subsystem 126 of the control unit 120 (FIG. 2) can use this electrical signal to determine a magnitude of an axial component of the contact force. The magnitude of the axial component of the contact force can be calculated using Hooke's law, wherein the displacement of an elastic element (e.g., elastic element 342) is proportional to the forced placed on element, based on a predetermined constant. Only the magnitude of the axial component of the contact force exerted on the distal end is determined by the force sensing subsystem 126 because there is only one position sensor 144 and it is disposed along the longitudinal axis of the elastic element 142.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A system for determining a contact force, the system comprising:
   a catheter including:
      a proximal segment;
      a distal segment including:
         a plurality of tip electrodes including at least three radial electrodes disposed about a circumference of the distal segment, the radial electrodes configured to output electrical signals indicative of a contact vector of the contact force; and
      an elastic segment extending from the proximal segment to the distal segment, the elastic segment including a force sensing device configured to output an electrical signal indicative of a magnitude of an axial component of the contact force, the force sensing device consisting of an elastic element and a position sensor; and
   control circuitry configured to:
      receive electrical signals from each of the plurality of tip electrodes;
      determine individual vectors for each of the plurality of tip electrodes based on their respective electrical signals;
      determine the contact vector of the contact force by summing the individual vectors for each of the plurality of tip electrodes;
      receive electrical signals from the force sensing device;
      determine the magnitude of the axial component of the contact force based on the electrical signals received from the force sensing device; and
      determine the contact force by scaling the magnitude of the axial component of the contact force by the contact vector.

2. The system of claim 1, wherein the plurality of tip electrodes further includes at least one axial electrode disposed at a distal end of the distal segment, the axial electrode configured along with the radial electrodes to output electrical signals indicative of the contact vector of the contact force.

3. The system of claim 1, wherein the elastic element has a longitudinal axis, the elastic element configured to mechanically support the distal segment in a base orientation with respect to the proximal segment, compress when the distal segment moves relative to the proximal segment in response to the application of the contact force, and resiliently return the distal segment to the base orientation with respect to the proximal segment once the contact force has been removed.

4. The system of claim 3, wherein the position sensor is disposed along the longitudinal axis of the elastic element and is configured to output a signal indicative of relative axial movement between the proximal segment and the distal segment.

5. The system of claim 1, wherein the individual vectors for each of the plurality of tip electrodes includes a magnitude and a direction for a corresponding tip electrode.

6. The system of claim 1, wherein the control circuitry is further configured to cause at least one of the plurality of tip electrodes to provide a current external to the distal segment, and the magnitude of each of the individual vectors includes a voltage.

7. The system of claim 1, further including a user interface having a display, wherein the control circuitry is further configured to graphically indicate on the display the magnitude and the direction of the contact force.

8. A method of determining a contact force exerted on a catheter having an elastic segment disposed between proximal and distal segments, the distal segment including a plurality of mapping electrodes and the elastic segment including an axial force sensing device, the method comprising:
   receiving electrical signals from each of the plurality of mapping electrodes;
   determining individual vectors for each of the plurality of mapping electrodes based on their respective electrical signals;
   determining a contact vector of the contact force by summing the individual vectors for each of the plurality of mapping electrodes;
   receiving electrical signals from the axial force sensing device;
   determining the magnitude of an axial component of the contact force based on the electrical signals received from the axial force sensing device; and
   determining the contact force by scaling the magnitude of the axial component of the contact force by the contact vector.

9. The method of claim 8, wherein determining the individual vectors for each of the plurality of mapping electrodes includes determining a magnitude and a direction for a corresponding mapping electrode.

10. The method of claim 8, further including causing at least one of the plurality of mapping electrodes to provide a current external to the distal segment, wherein the magnitude determined for each of the individual vectors includes a voltage.

11. The method of any of claim 8, further including causing a display device to present a representation of the catheter and the contact force.

12. The method of any of claim 8, further including filtering the received electrical signals from each of the plurality of mapping electrodes to remove electrical signals from an ablation procedure.

* * * * *